United States Patent [19]

Maurer et al.

[11] Patent Number: 4,521,420

[45] Date of Patent: Jun. 4, 1985

[54] OXOQUINAZOLINE CARBAMATES

[75] Inventors: Fritz Maurer, Wuppertal; Wilhelm Brandes, Leichlingen; Karl-Heinz Kuck, Langenfeld; Paul Reinecke; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 518,867

[22] Filed: Aug. 1, 1983

[30] Foreign Application Priority Data

Aug. 3, 1982 [DE] Fed. Rep. of Germany ....... 3228871

[51] Int. Cl.[3] .................. A61K 31/505; C07D 239/90

[52] U.S. Cl. .................................. 514/259; 544/285; 544/287; 544/289; 548/404

[58] Field of Search ...................... 544/287, 285, 289; 424/251

[56] References Cited

FOREIGN PATENT DOCUMENTS 956635 10/1974 Canada .............................. 544/287

1153481 5/1969 United Kingdom .

*Primary Examiner*—Glennon H. Hollrah

*Assistant Examiner*—James H. Turnipseed

*Attorney, Agent, or Firm*—Sprung, Horn, Kramer & Woods

[57] ABSTRACT

An oxoquinazoline carbamate of the formula

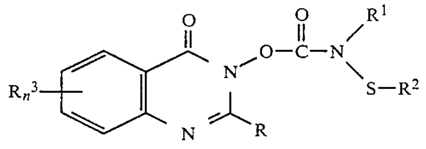

in which

R represents hydrogen, alkyl, alkoxy, alkoxyalkyl, alkylthio, alkylthioalkyl, halogenoalkyl or optionally substituted aryl, $R^1$ represents alkyl, $R^2$ represents halogenoalkyl, $R^3$ represents alkyl or halogen and n represents a number from 0 to 4, which possess fungicidal and microbicidal activity.

9 Claims, No Drawings

OXOQUINAZOLINE CARBAMATES

The invention relates to new oxoquinazoline carbamates, a process for their preparation and their use as pest-combating agents.

It has already been disclosed that a number of inorganic and organic chemical compounds, such as, for example, basic copper chloride or zinc ethylene-1,2-bis-(dithiocarbamate) or N-trichloromethylthio-tetrahydro-phthalimide, possess fungicidal and bactericidal properties. (See, for example, R. Wegler, "Chemie der Pflanzenschutz-and Schädlingsbekämpfungsmittel" [Chemistry of Plant Protection Agents and Pest-Combating Agents], Springer Verlag Berlin, Volume 2.) However, the action is not always completely satisfactory, in particular when low amounts and concentrations are used.

New oxoquinazoline carbamates of the general formula (I)

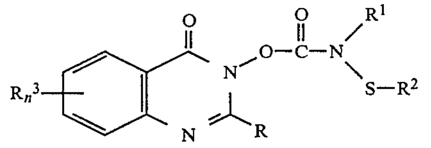
(I)

in which

R represents hydrogen, alkyl, alkoxy, alkoxyalkyl, alkylthio, alkylthioalkyl, halogenoalkyl or optionally substituted aryl, $R^1$ represents alkyl, $R^2$ represents halogenoalkyl, $R^3$ represents alkyl or halogen and n represents a number from 0 to 4, have been found.

Furthermore, it has been found that the new oxoquinazoline carbamates of the formula (I)

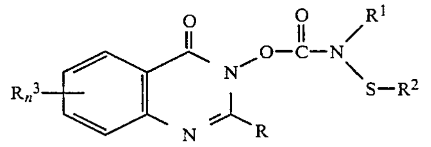
(I)

in which

R represents hydrogen, alkyl, alkoxy, alkoxyalkyl, alkylthio, alkylthioalkyl, halogenoalkyl or optionally substituted aryl, $R^1$ represents alkyl, $R^2$ represents halogenoalkyl, $R^3$ represents alkyl or halogen and n represents a number from 0 to 4, are obtained when 3-hydroxy-4-oxo-3,4-dihydroquinazolines of the formula (II)

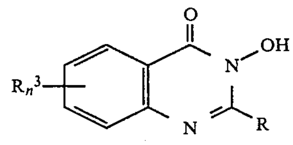
(II)

in which R, $R^3$ and n have the meaning given above, are reacted with carbamoyl halides of the formula (III)

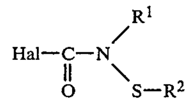
(III)

in which $R^1$ and $R^2$ have the meaning given above and

HaL represents halogen, in the presence of an acid-binding agent and, if appropriate, in the presence of a diluent.

The new oxoquinazoline carbamates of the formula (I) possess powerful fungicidal and bactericidal properties.

In this respect, the compounds according to the invention, of the formula (I), surprisingly exhibit better fungicidal and bactericidal activity than the fungicidal substances known from the prior art: zinc ethylene-1,2-bis-(dithiocarbamate) or N-trichloromethylthiotetrahydrophthalimide or, as a known bactericidal substance, basic copper chloride. The substances according to the invention thus represent an enrichment of the art.

Formula (I) gives a general definition of the oxoquinazoline carbamates according to the invention. In this formula, R preferably represents hydrogen, straight-chain or branched alkyl, alkoxy, alkoxyalkyl, alkylthio or alkylthioalkyl, each having up to 6 carbon atoms per alkyl radical, halogenoalkyl having up to 3 carbon atoms and up to 7 identical or different halogen atoms, in particular fluorine, chlorine or bromine, and aryl which has 6 to 10 carbon atoms and is optionally monosubstituted or polysubstituted by identical or different substituents, suitable substituents being: alkyl having up to 4 carbon atoms, halogenoalkyl having up to 3 carbon atoms and up to 5 halogen atoms, and halogen, in particular fluorine, chlorine or bromine, $R^1$ preferably represents straight-chain or branched alkyl having up to 6 carbon atoms, $R^2$ preferably represents halogenoalkyl having up to 3 carbon atoms and up to 7 identical or different halogen atoms, in particular fluorine, chlorine or bromine, $R^3$ preferably represents straight-chain or branched alkyl having up to 4 carbon atoms, or halogen, in particular fluorine, chlorine or bromine, and n preferably represents a number from 0 to 3.

Particularly preferred compounds of the formula (I) are those in which

R represents hydrogen, straight-chain or branched alkyl having 1 to 4 carbon atoms, such as methyl ethyl, isopropyl, n-propyl, n-butyl, isobutyl, sec.-butyl or tert.-butyl, alkoxy having 1 to 4 carbon atoms, such as methoxy, ethoxy, n-propoxy, isopropoxy or n-butoxy, alkoxyalkyl having 1 to 4 carbon atoms per alkyl radical, such as methoxymethyl, ethoxymethyl, n-propoxymethyl, isopropoxymethyl, n-butoxymethyl, isobutoxymethyl, sec.-butoxymethyl, tert.-butoxymethyl, 2-methoxyethyl, 2-ethoxyethyl, 2-n-propoxyethyl, 2-isopropoxyethyl, 2-n-butoxyethyl, 2-isobutoxyethyl, 2-tert.-butoxy-ethyl, 2-sec.-butoxyethyl, 2-methoxy-n-propyl, 2-ethoxy-n-propyl, 2n-propoxy-n-propyl, 2-iso-propoxy-n-propyl- or 4-methoxy-n-butyl, alkylthio having 1 to 4 carbon atoms, such as methylthio, ethylthio, n-propylthio, isopropylthio, n-butylthio, isobutylthio, sec.-butylthio or tert.-butylthio, alkylthioalkyl having 1 to 4 carbon atoms per alkyl radical, such as methylthiomethyl, ethyl thiomethyl, n-propylthiomethyl, isopropylthio methyl, n-butylthiomethyl, isobutylthiomethyl, sec.-butylthiomethyl, tert.-butylthiomethyl, 2-methylthioethyl, 2-ethylthioethyl, 2-n-propylthioethyl, 2-isopropylthioethyl, 2-n-butylthioethyl, 2-isobutylthioethyl, 2-tert.-butylthioethyl, 3-methylthio-n-propyl, 3-ethylthio-n-propyl, 3-n-propylthio-n-propyl, 3-isopropylthio-n-propyl, 3-n-butylthio-n-propyl, 3-tert.-butylthio-n-propyl, 4-methylthio-n-butyl or 4-ethylthio-n-butyl, halogenoalkyl having 1 to 2 carbon atoms and 1 to 5 identical or different halogen atoms, in particular fluorine, chlorine or bromine, such as, for example, trichloromethyl, trifluoromethyl, dichlorofluoromethyl, chlorodifluoromethyl or pentachloroethyl, and phenyl which is optionally monosubstituted to trisubstituted by identical or different substituents, particularly preferred substituents being: fluorine, chlorine, bromine, methyl, ethyl, trifluoromethyl and trichloromethyl, $R^1$ represents straight-chain or branched alkyl having 1 to 4 carbon atoms, such as methyl, ethyl, n-propyl, isopropyl, n-butyl, isobutyl, sec.-butyl or tert.-butyl, $R^2$ represents halogenoalkyl having 1 to 2 carbon atoms and 1 to 5 identical or different halogen atoms, in particular fluorine, chlorine or bromine, such as trichloromethyl, trifluoromethyl, dichlorofluoromethyl, chlorodifluoromethyl or pentachloroethyl, $R^3$ represents methyl, ethyl, fluorine, chlorine or bromine and n represents the number 0, 1 or 2.

In addition to the compounds listed in the preparation examples, the following compounds of the formula (I) may be mentioned individually:

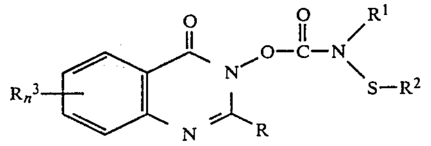

(I)

| R | $R^1$ | $R^2$ | $R^3$ | n |
|---|---|---|---|---|
| $-CH_3$ | $-CH_3$ | $-CCl_3$ | — | 0 |
| $-CH_3$ | $-C_2H_5$ | $-CCl_2F$ | — | 0 |
| $-CH_3$ | $n-C_3H_7-$ | $-CCl_2F$ | — | 0 |
| $-CH_3$ | $i-C_3H_7-$ | $-CCl_2F$ | — | 0 |
| $-CH_3$ | $n-C_4H_9-$ | $-CCl_2F$ | — | 0 |
| $-CH_3$ | $i-C_4H_9-$ | $-CCl_2F$ | — | 0 |
| $-CH_3$ | $t-C_4H_9-$ | $-CCl_2F$ | — | 0 |
| $n-C_3H_7-$ | $-CH_3$ | $-CCl_2F$ | — | 0 |
| $i-C_3H_7-$ | $-CH_3$ | $-CCl_2F$ | — | 0 |
| $-OCH_3$ | $-C_2H_5$ | $-CCl_2F$ | — | 0 |
| $-OC_2H_5$ | $-CH_3$ | $-CCl_2F$ | — | 0 |
| $-CH_2Cl$ | $-CH_3$ | $-CCl_2F$ | — | 0 |
| $-CHCl_2$ | $-CH_3$ | $-CCl_2F$ | — | 0 |
| $-CF_3$ | $-CH_3$ | $-CCl_2F$ | — | 0 |
| $-CCl_3$ | $-CH_3$ | $-CCl_2F$ | — | 0 |
| $-CH_2-SCH_3$ | $-CH_3$ | $-CCl_2F$ | — | 0 |
| $-C_6H_5$ | $-CH_3$ | $-CCl_3$ | — | 0 |
| $-C_6H_5$ | $-C_2H_5$ | $-CCl_2F$ | — | 0 |
| 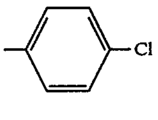 | $-CH_3$ | $-CCl_2F$ | — | 0 |

-continued

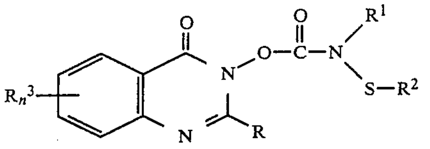

(I)

| R | $R^1$ | $R^2$ | $R^3$ | n |
|---|---|---|---|---|
| 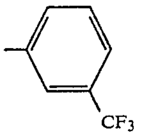 | $-CH_3$ | $-CCl_2F$ | — | 0 |
| $-CH_3$ | $-CH_3$ | $-CCl_3$ | $CH_3$ | 1 |
| $-CH_3$ | $-C_2H_5$ | $-CCl_2F$ | $CH_3$ | 1 |
| $-CH_3$ | $n-C_3H_7-$ | $-CCl_2F$ | $CH_3$ | 1 |
| $-CH_3$ | $i-C_3H_7-$ | $-CCl_2F$ | $CH_3$ | 1 |
| $-CH_3$ | $n-C_4H_9-$ | $-CCl_2F$ | $C_2H_5$ | 1 |
| $-CH_3$ | $i-C_4H_9-$ | $-CCl_2F$ | $C_2H_5$ | 1 |
| $-CH_3$ | $t-C_4H_9-$ | $-CCl_2F$ | F | 1 |
| $n-C_3H_7$ | $-CH_3$ | $-CCl_2F$ | F | 1 |
| $i-C_3H_7$ | $-CH_3$ | $-CCl_2F$ | Cl | 1 |
| $-OCH_3$ | $-C_2H_5$ | $-CCl_2F$ | Cl | 1 |
| $-OC_2H_5$ | $-CH_3$ | $-CCl_2F$ | $CH_3$ | 1 |
| $-CH_2Cl$ | $-CH_3$ | $-CCl_2F$ | Br | 1 |
| $-CHCl_2$ | $-CH_3$ | $-CCl_2F$ | Br | 1 |
| $-CF_3$ | $-CH_3$ | $-CCl_2F$ | Br | 1 |
| $-CCl_3$ | $-CH_3$ | $-CCl_2F$ | $C_2H_5$ | 1 |
| $-CH_2-SCH_3$ | $-CH_3$ | $-CCl_2F$ | $C_2H_5$ | 1 |
| $-C_6H_5$ | $-CH_3$ | $-CCl_3$ | $C_2H_5$ | 1 |
| $-C_6H_5$ | $-C_2H_5$ | $-CCl_2F$ | $CH_3$ | 1 |
| 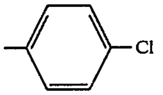 | $-CH_3$ | $-CCl_2F$ | $C_2H_5$ | 1 |
| 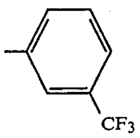 | $-CH_3$ | $-CCl_2F$ | $C_2H_5$ | 1 |

If, for example, 2-ethyl-3-hydroxy-3,4-dihydro-4-oxo-quinazoline and N-methyl-N-dichlorofluoromethylsulphenyl-carbamoyl fluoride are used as starting materials, the course of the reaction of the process according to the invention can be represented by the following equation:

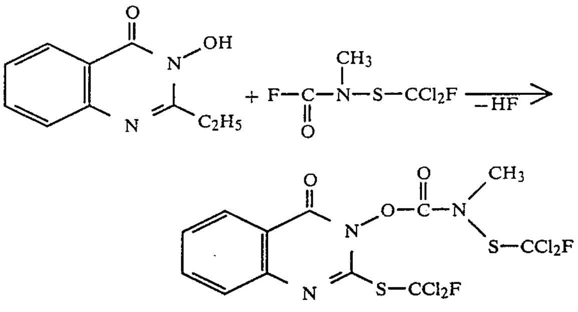

Formula (II) gives a general definition of the 3-hydroxy-4-oxo-3,4-dihydroquinazolines to be used as starting materials in carrying out the process according to the invention. In this formula, R, $R^3$ and n preferably represent those radicals which have already been mentioned in connection with the description of the substances according to the invention, of the formula (I), as being preferred for these substituents.

Hydroxy-4-oxo-3,4-dihydroquinazolines of the formula (II) are known (see, for example, C. B. Schapira and S. Lamdan, J. Heterocycl. Chem. 9, 569 (1972)).

They are obtained, for example, by subjecting o-aminobenzhydroxamic acids of the formula (IV)

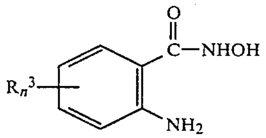

(IV)

in which $R^3$ and n have the meaning given above, to a cyclization reaction with acylating agents, such as, for example, acyl halides or carboxylic acid ortho-esters, in the presence of a solvent, at temperatures between 20° C. and 150° C., if appropriate in the presence of a catalyst.

The o-aminobenzhydroxamic acids of the formula (IV) are known (see, for example, A. W. Scott and B. L. Wood, J. Org. Chem. 7, 508 (1942)).

Formula (III) gives a general definition of the carbamoyl halides furthermore to be used as starting materials. In this formula, $R^1$ and $R^2$ preferably represent those radicals which have already been mentioned in connection with the description of the substances according to the invention, of the formula (I), as being preferred for these substituents. Hal preferably represents fluorine or chlorine.

The carbamoyl halides of the formula (III) are known (see, for example, Belgian Pat. No. 717,705).

Preferred diluents for the reaction according to the invention are all inert organic solvents. These include, in particular, aliphatic and aromatic, optionally chlorinated hydrocarbons, such as benzine, benzene, toluene, xylene, methylene chloride, chloroform, carbon tetrachloride, chlorobenzene and o-dichlorobenzene, ethers, such as diethyl ether, diisopropyl ether, dioxane and tetrahydrofuran, ketones, such as acetone, butanone, methyl isopropyl ketone and methyl isobutyl ketone, nitriles, such as acetonitrile and propionitrile, and the highly polar solvents dimethylsulphoxide and hexamethylphosphoric acid triamide.

The process according to the invention is carried out in the presence of acid-binding agents. All inorganic and organic acid-binding agents which can customarily be used can be added. These preferably include alkali metal carbonates, such as, for example, sodium carbonate, potassium carbonate and sodium bicarbonate, and also lower tertiary alkylamines, cycloalkylamines or arylalkylamines, such as, for example, triethylamine, N,N-dimethyl-benzyl-amine, and furthermore pyridine and 1,4-diazabicyclo[2.2.2]octane and 1,5-diazabicyclo[4.3.0]non-5-ene.

In carrying out the process according to the invention, the reaction temperature can be varied within a relatively wide range. In general, the reaction is carried out at between 0° C. and 100° C., preferably between 10° C. and 80° C.

The process according to the invention is carried out in general under atmospheric pressure.

To carry out the process according to the invention, between 1 and 1.5 mols, preferably between 1 and 1.2 mols, of carbamoyl halide of the formula (III) are usually employed per mol of 3-hydroxy-4-oxo-3,4-dihydroquinazoline of the formula (II).

The reaction is preferably carried out using one of the abovementioned acid-binding agents in one of the diluents given above. The reaction mixture is stirred for several hours at the required temperature. Working-up of the reaction mixture and isolation of the reaction products according to the invention, of the formula (I), are effected in a generally customary manner.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention, of the formula (I), can be used with particularly good success for combating Botrytis species, such as, for example, the grey mould of fruits causative organism (*Botrytis cinerea*) for combating Leptosphaeria species, such as, for example the Leaf spot of wheat causative organism (*Leptosphaeria nodorum*) and for combating Xanthomonas species, such as, for example, the stripe disease of rice causative organism (*Xanthomonas oryzae*), as well as for combating cereal rust and rice diseases, such as, for example, *Pyricularia oryzae*.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes of methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water: by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001to 0.1% by weight, preferably 0.0001 to 0.2% by weight, are required at the place of action.

Preparation examples

EXAMPLE 1

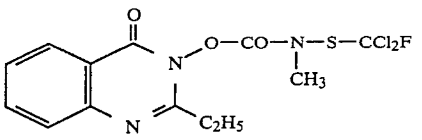

A mixture of 19 g (0.1 mol) of 2-ethyl-3-hydroxy-3,4-dihydro-4-oxo-quinazoline, 20.6 g (0.15 mol) of potassium carbonate, 200 ml of acetonitrile and 21 g (0.1 mol) of N-methyl-N-dichlorofluoromethylsulphenylcarbamoyl fluoride is stirred for 30 minutes at 40° C. After the mixture has been cooled to room temperature, 300 ml of toluene are added and the mixture is then extracted by shaking with twice 300 ml of water. The organic phase is dried over sodium sulphate and evaporated down in vacuo. 29.6 g (78% of theory) of N-methyl N-dichlorofluoromethylsulphenyl O-(2-ethyl-3,4-dihydro-4-oxo-quinazolin-3-yl)carbamate remain in the form of colorless crystals of melting point 100° C.

The following compounds of the formula (I)

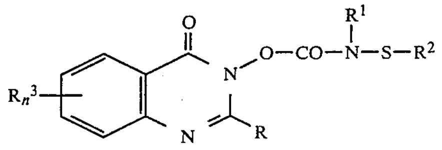

(I)

can be prepared analogously:

| Example No. | R | $R^1$ | $R^2$ | $R^3$ | n | Melting point ° C. |
|---|---|---|---|---|---|---|
| 2 | $CH_3$ | $CH_3$ | $CCl_2F$ | — | 0 | 106 |
| 3 | 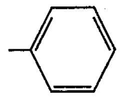 | $CH_3$ | $CCl_2F$ | — | 0 | 57 |
| 4 | $OCH_3$ | $CH_3$ | $CCl_2F$ | — | 0 | 90 |
| 5 | 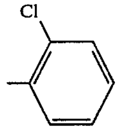 | $CH_3$ | $CCl_2F$ | — | 0 | 128 |
| 6 | 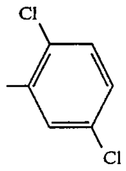 | $CH_3$ | $CCl_2F$ | — | 0 | 166 |

Preparation of the starting materials:

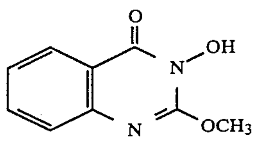

(a)

A mixture of 22.8 g (0.15 mol) of o-amino-benzhydroxamic acid, 50 ml of methanol and 27.2 g (0.2 mol) of tetramethyl orthocarbonate is boiled under reflux for 2 hours and then cooled to 5° C. The product which crystallizes out is filtered off under suction. In this manner, 17 g (60% of theory) of 2-methoxy-3-hydroxy-3,4-dihydro-4-oxo-quinazoline are obtained in the form of colorless crystals of melting point 220° C.

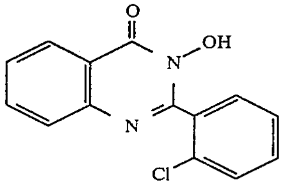

(b)

35 g (0.2 mol) of o-chlorobenzoyl chloride are added to a solution of 30.4 g (0.2 mol) of o-aminobenzhydroxamic acid in 250 ml of dioxane at 20°-30° C. The mixture is boiled under reflux for 3 hours, the solvent is then distilled in vacuo, 100 ml of ether are added to the residue, and the crystalline product is filtered off under suction. It is dissolved in 300 ml of 5% strength sodium hydroxide solution, the solution is filtered and the filtrate is acidified with concentrated hydrochloric acid. The precipitated product is then filtered off under suction and rinsed with water. In this manner, 28.2 g (52% of theory) of 2-(2-chlorophenyl)-3-hydroxy-3,4-dihydro-4-oxo-quinazoline are obtained in the form of crystals of melting point 211° C.

The following compounds of the formula (II)

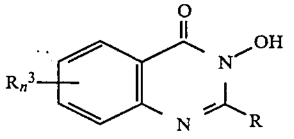

(II)

can be prepared analogously:

| R | n | $R^3$ | Melting point °C. |
|---|---|---|---|
| (c) $-OC_2H_5$ | O | — | 154 |
| (d) $-CH_3$ | O | — | 215 |
| (e) $-C_2H_5$ | O | — | 150 |
| (f) $-H$ | O | — | 244 |
| (g) $-CH_2-S-CH_3$ | O | — | 171 |
| (h) iso-$C_3H_7-$ | O | — | 61 |
| (i) n-$C_3H_7-$ | O | — | 150 |
| (j) 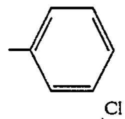 | O | — | 177 |
| (k) 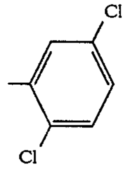 | O | — | 213 |

Use examples

The compounds indicated here are employed as comparative substances in the examples which follow.

$Cu(OH)_2.CuCl_2.H_2O$ (A)

basic copper chloride hydrate

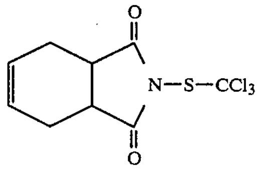

(B)

N-trichloromethylthio-tetrahydrophthalimide

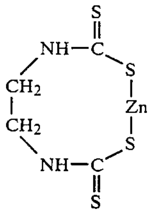

(C)

zinc ethylene-1,2-bis-(dithiocarbamate)

EXAMPLE A

*Xanthomonas oryzae* test/bacteriosis/rice/systemic

Solvent: 121.25 parts by weight of acetone

Emulsifier: 3.75 parts by weight of alkylaryl polyglycol ether

To produce a suitable preparation of active compound, 1 part by weight of active compound is mixed with the stated amounts of solvent and emulsifier, and the concentrate diluted with water to the desired concentration.

To test for systemic properties, standard soil in which young plants have been grown in watered with 100 ml of the preparation of active compound. 3 days after the treatment, the plants are inoculated with an aqueous suspension of *Xanthomonas oryzae* by pricking. Thereafter, the plants remain in a greenhouse at 24° to 26° C. and 70 to 80% relative atmospheric humidity for 14 days until they are evaluated.

In this test, a clearly superior activity compared with the prior art is shown, for example, by the compound according to the following preparation example: 4.

EXAMPLE B

Botrytis test (bean)/protective

Solvent: 4.7 parts by weight of acetone

Emulsifier: 0.3 parts by weight of alkylaryl polyglycol ether

To produce a suitable preparation of active compound 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to the following preparation examples : 1, 2, 3 and 4.

EXAMPLE C

*Leptosphaeria nodorum* test (wheat)/protective

Solvent: 100 parts by weight of dimethylformamide

Emulsifier: 0.25 parts by weight of alkylaryl polyglycol ether

To produce a suitable preparation of active compound 1, part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum.* The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compounds according to the following preparation examples: 1, 2, 3, 4, 5 and 6.

It will be appreciated that the instant specification and examples are set forth by way of illustration and not limitation, and that various modifications and changes may be made without departing from the spirit and scope of the present invention.

We claim:

1. An oxoquinazoline carbamate of the formula

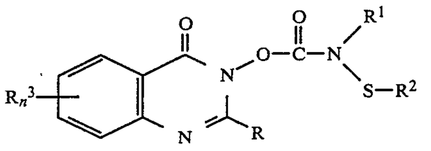

in which

R represents hydrogen, straight-chain or branched alkyl, alkoxy, alkoxyalkyl, alkylthio or alkylthioalkyl, each having up to 6 carbon atoms per alkyl radical, halogenoalkyl having up to 3 carbon atoms and up to 7 identical or different halogen atoms, or aryl which has 6 to 10 carbon atoms and is optionally monosubstituted or polysubstituted by identical or different substituents selected from alkyl having up to 4 carbon atoms, halogenoalkyl having up to 3 carbon atoms and up to 5 halogen atoms, and halogen, $R^1$ represents straight-chain or branched alkyl having up to 6 carbon atoms, $R^2$ represents halogenoalkyl having up to 3 carbon atoms and up to 7 identical or different halogen atoms, $R^3$ represents straight-chain or branched alkyl having up to 4 carbon atoms, or halogen, and n represents a number from 0 to 3.

2. An oxoquinazoline carbamate according to claim 1, wherein

R represents hydrogen, straight-chain or branched alkyl, alkoxy, alkoxyalkyl, alkylthio or alkylthioalkyl, each having 1 to 4 carbon atoms per alkyl radical, halogenoalkyl having 1 to 2 carbon atoms and 1 to 5 identical or different halogen atoms, or phenyl which is optionally monosubstituted to trisubstituted by identical or different substituents selected from fluorine, chlorine, bromine, methyl, ethyl, trifluoromethyl and trichloromethyl, $R^1$ represents straight-chain or branched alkyl having 1 to 4 carbon atoms, $R^2$ represents halogenoalkyl having 1 to 2 carbon atoms and 1 to 5 identical or different halogen atoms, $R^3$ represents methyl, ethyl, fluorine, chlorine or bromine, and n represents the number 0, 1 or 2.

3. A compound according to claim 1, wherein such compound is N-methyl N-dichlorofluoromethylsulphenyl O-(2-ethyl-3,4-dihydro-4-oxo-quinazolin-3-yl) carbamate of the formula

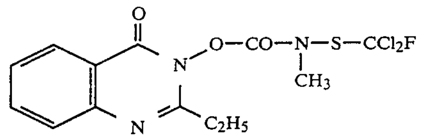

4. A compound according to claim 1, wherein such compound is N-methyl N-dichlorofluoromethylsulphenyl O-(2-methyl-3,4-dihydro-4-oxo-quinazolin-3-yl) carbamate of the formula

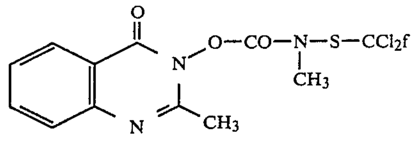

5. A compound according to claim 1, wherein such compound is N-methyl N-dichlorofluoromethylsulphenyl O-(2-phenyl-3,4-dihydro-4-oxo-quinazoline-3-yl) carbamate of the formula

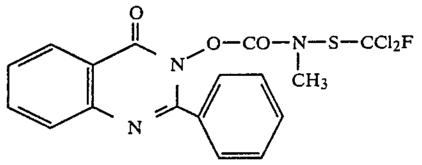

6. A compound according to claim 1, wherein such compound is N-methyl N-dichlorofluoromethylsulphenyl O-(2-methoxy-3,4-dihydro-4-oxo-quinazoline-3-yl) carbamate of the formula

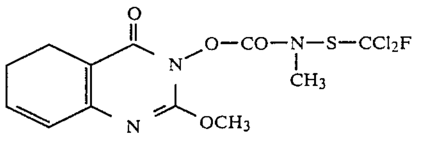

7. A fungicidal composition comprising a fungicidally effective amount of a compound according to claim 1 in admixture with a diluent.

8. A method of combatting fungi which comprises administering to such fungi or to a fungus habitat a fungicidally effective amount of a compound according to claim 1.

9. The method according to claim 8, wherein such compound is

N-methyl N-dichlorofluoromethylsulphenyl O-(2-ethyl-3,4-dihydro-4-oxo-quinazolin-3-yl) carbamate, N-methyl N-dichlorofluoromethylsulphenyl O-(2-methyl-3,4-dihydro-4-oxo-quinazolin-3-yl) carbamate, N-methyl N-dichlorofluoromethylsulphenyl O-(2-phenyl-3,4-dihydro-4-oxo-quinazolin-3-yl) carbamate, or N-methyl N-dichlorofluoromethylsulphenyl O-(2-methoxy-3,4-dihydro-4-oxo-quinazolin-3-yl) carbamate.

* * * * *

UNITED STATES PATENT AND TRADEMARK OFFICE
CERTIFICATE OF CORRECTION

PATENT NO. : 4,521,420

DATED : June 4, 1985

INVENTOR(S) : Fritz Maurer, et al

It is certified that error appears in the above-identified patent and that said Letters Patent is hereby corrected as shown below:

| | |
|---|---|
| Col. 1, line 13 | Delete "-and" and substitute -- -und-- |
| Col. 2, line 9 | Delete "HaL" and substitute --Hal-- |
| Col. 2, line 65 | Delete "2n-" and substitute -- 2-n- -- |
| Col. 3, line 14 | After "1" delete "to" and substitute --or-- |
| Col. 4, line 64 | Bottom right of formula delete "$CCl_2F$" and substitute --$C_2H_5$-- |
| Col. 6, line 62 | Delete "of" and substitute --or-- |
| Col. 10, line 32 | After "concentrate" insert --is-- |
| Col. 10, line 35 | After "grown" delete "in" and substitute --is-- |
| Col. 10, lines 51, 52 | After "compound" insert --,-- |
| Col. 11, line 67 and Col. 12, line 7 | Delete "to" before"2" and substitute --or-- |
| Col. 12, line 33 | End of formula delete "$CCl_2f$" and substitute --$CCl_2F$-- |

UNITED STATES PATENT AND TRADEMARK OFFICE

CERTIFICATE OF CORRECTION

PATENT NO. : 4,521,420

DATED : June 4, 1985

INVENTOR(S) : Fritz Maurer, et al

It is certified that error appears in the above-identified patent and that said Letters Patent is hereby corrected as shown below:

Col. 12, line 58 Delete beginning of formula and substitute:

-- 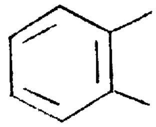 --

Signed and Sealed this

*Fifteenth* Day of *October 1985*

[SEAL]

*Attest:*

DONALD J. QUIGG

*Attesting Officer*

*Commissioner of Patents and Trademarks—Designate*